(12) United States Patent
Carlucci et al.

(10) Patent No.: US 7,105,715 B2
(45) Date of Patent: Sep. 12, 2006

US007105715B2

(54) ABSORBENT ARTICLE PERFORMING COLOR CHANGE IN RESPONSE TO EXTERNAL STIMULUS

(75) Inventors: Giovanni Carlucci, Chieti (IT); Carlo Toro, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/118,795

(22) Filed: Apr. 29, 2005

(65) Prior Publication Data

US 2005/0256479 A1    Nov. 17, 2005

(30) Foreign Application Priority Data

Apr. 30, 2004   (EP)   .................... 0410870

(51) Int. Cl.
*A61F 13/15*   (2006.01)
*A61F 13/20*   (2006.01)

(52) U.S. Cl. .................. 604/361; 604/385.01; 604/359

(58) Field of Classification Search ............... 604/361, 604/385.1, 378, 385.01; 446/153, 14; 374/141
See application file for complete search history.

(56) References Cited

U.S. PATENT DOCUMENTS

| | | |
|---|---|---|
| 2,681,032 A | 6/1954 | Shaw |
| 4,121,011 A | 10/1978 | Glover et al. |
| 4,826,550 A | 5/1989 | Shimizu et al. |
| 5,221,288 A | 6/1993 | Kamada et al. |
| 5,389,093 A | 2/1995 | Howell |
| 5,730,961 A | 3/1998 | Goudjil |
| 6,080,415 A | 6/2000 | Simon |
| 6,306,409 B1 | 10/2001 | Ogawa et al. |
| 6,330,730 B1 | 12/2001 | Davies et al. |
| 6,399,853 B1 * | 6/2002 | Roe et al. .................. 604/362 |
| 6,562,297 B1 | 5/2003 | Bonstein et al. |
| 6,635,797 B1 | 10/2003 | Olson et al. |
| 6,710,221 B1 * | 3/2004 | Pierce et al. ............... 604/361 |
| 6,872,444 B1 * | 3/2005 | McDonald et al. ......... 428/206 |
| 2002/0169427 A1 | 11/2002 | Roe et al. |
| 2003/0014025 A1 * | 1/2003 | Allen et al. ................. 604/361 |
| 2003/0120227 A1 * | 6/2003 | Williams .................... 604/361 |
| 2004/0087922 A1 * | 5/2004 | Bobadilla ................... 604/361 |
| 2004/0172000 A1 * | 9/2004 | Roe et al. ................... 604/361 |
| 2005/0133401 A1 * | 6/2005 | Lange ........................ 206/581 |
| 2005/0177120 A1 * | 8/2005 | Olson et al. ............... 604/361 |

FOREIGN PATENT DOCUMENTS

| | | |
|---|---|---|
| EP | 610072 | 8/1994 |
| JP | 7034394 | 2/1995 |

OTHER PUBLICATIONS

Arsenault et al. "From Colour Fingerprinting to the Control of Photoluminescence in Elastic Photonic Crystals" (Nature Materials, 5, 178-184 (2006)).*
PCT International Search Report dated Aug. 12, 2005.

* cited by examiner

*Primary Examiner*—Tatyana Zalukaeva
*Assistant Examiner*—Melanie J. Hand
(74) *Attorney, Agent, or Firm*—Gary J. Foose; Roddy M. Bullock; David M. Weirich

(57) ABSTRACT

The present invention relates to the field of absorbent articles for feminine hygiene. The absorbent articles of the present invention are capable to perform colour changes in response to an external stimulus. These colour changes are visible to the users of such articles. The external stimuli herein are pressure, temperature and light.

2 Claims, No Drawings

ABSORBENT ARTICLE PERFORMING COLOR CHANGE IN RESPONSE TO EXTERNAL STIMULUS

CROSS REFERENCE TO RELATED APPLICATIONS

1. Field of Invention

The present invention relates to the field of absorbent articles for feminine hygiene. The absorbent articles of the present invention are capable to perform colour changes in response to an external stimulus. These colour changes are visible to the users of such articles. The external stimuli herein are pressure, temperature and light.

2. Background of the Invention

Today's fashion trends are becoming more and more holistic and it is also well known that today's consumers have an appetite for new experiences. Especially younger women are very trend-oriented and are attempting to create environments for themselves, which are styled according to the latest trend in a holistic manner. Such consumers are ever increasingly searching for special effects and original colours.

Absorbent articles for personal hygiene are designed in a very functional way. With very rare exceptions, such as black panty liners or tanga liners, such articles do not comprise any fashion- or fun elements. Commercially available absorbent articles like sanitary pads or panty liners are still typically white. This does not reflect the above-described trends in terms of holistic fashion.

Thus there exists the need for absorbent articles of feminine hygiene, which are more in line with current fashion and lifestyle trends. In particular, there is a need for such articles, which include fun elements and which are in a way responsive to the user.

There are absorbent articles known in the art, which undergo colour changes during use. U.S. Pat. No. 5,389,093 discloses a diaper with a wetness indicator. The wetness indicator is printed artwork visible through the backsheet of the diaper, which artwork is printed by water-soluble ink. Upon urination into the diaper the artwork disappears as the water-soluble ink dissolves.

Another similar approach is U.S. Pat. No. 6,635,797, which discloses a diaper indicating urination by colour change of a thermochromic ink. This document is focused on a diaper for being used for toilet training for infants by indicating urination into the diaper through appearing/disappearing patterns/decoration visible to its outsides.

There is furthermore a great variety of surgical garments in the art, which include indicators for certain microbes or substances, which change their colour at a certain pH value.

All these articles are not suited for being used by younger, trend-sensitive women. Further, all these articles do not comprise any fashion elements and are not suited to a trendy environment.

SUMMARY OF THE INVENTION

The present invention satisfies this need by providing absorbent articles for feminine hygiene, which change colour in response to external stimuli, particularly light, pressure or temperature.

According to another preferred embodiment of the present invention the articles simultaneously also release a pleasant odour to provide a multi-sensorial effect to the user.

In a further embodiment of the present invention the absorbent articles herein are packaged in a bag. This bag is also provided with the ability to respond to external stimuli by colour changes, particularly to light, pressure or temperature.

All documents cited are, in relevant part, incorporated herein by reference; the citation of any document is not to be construed as an admission that it is prior art with respect to the present invention.

BRIEF DESCRIPTION OF THE DRAWINGS

DETAILED DESCRIPTION OF THE DRAWINGS

The term 'absorbent article' herein refers to absorbent articles for feminine hygiene, i.e. sanitary pads, panty liners, tampons, incontinence pads, breast pads and the like. The absorbent articles of the present invention have a wearer- and a garment-facing surface and a peripheral edge. Typically the absorbent articles herein comprise a fluid pervious topsheet as the layer contacting the skin of the wearer in use, a fluid impervious backsheet, which is preferably, but not necessarily water vapour and/or gas pervious as the layer contacting the garment of the wearer in use, and an absorbent core, being positioned between the backsheet and the topsheet. Optionally a secondary topsheet can be placed between the topsheet and the absorbent core for further improving fluid acquisition performance of the article. All layers of the absorbent article (e.g. the topsheet, the backsheet and the absorbent core) have a wearer- and a garment-facing surface. Particularly preferred absorbent articles in the context of the present invention are disposable absorbent articles. The absorbent articles herein comprise at least one active region being provided with a colour change material for performing a colour change in response to an external stimulus, such that the colour change is noticeable to the user of said article.

The term 'disposable' is used herein to describe absorbent articles, which are not intended to be laundered or otherwise restored or reused as an article (i.e. they are intended to be discarded after a single use and preferably to be recycled, composted or otherwise disposed of in an environmentally compatible manner).

The term 'use', as used herein, refers to the period of time that starts when the absorbent article is actually put in contact with the anatomy of the user.

By 'body fluid' it is meant herein any water based fluids or liquids excreted from the human body such as urine, menses, serum, blood, sweat, mucous as well as other aqueous solutions generally defined as body fluids, but it is not intended to exclude other water based fluids.

The term 'bag' herein refers to a suitable package for at least one of the absorbent articles of the present invention. The bag herein can be made of any suitable material, such as plastic films, paper, cardboard, nonwovens or the like. The bag herein comprise at least one active region being provided with a colour change material for performing a colour change in response to an external stimulus, such that the colour change is noticeable to the user of said bag. The term bag herein comprises both an individual package for one absorbent article as well as a package for a plurality of absorbent articles, which may be individually packaged as well.

'Active region' herein means at least a portion of the absorbent article or the bag, which is provided with a colour change material, wherein said colour change material changes colour in response to an external stimulus. There can be one or more active region present on the absorbent article or bag.

In terms of the bag herein the active regions can be at any suitable location of the bag. In one embodiment the bag material is non-transparent and is provided with an active region comprising a pressure sensitive dye, which becomes transparent when the user touches it. The same result can be achieved by using a thermochromic dye because of the skin temperature. By this the user can have a look into the inside of the bag for viewing the absorbent articles packaged therein by just putting her finger on the active region of the bag.

In terms of the absorbent article herein, the active region can be located on the wearer- or on the garment-facing surface or between those surfaces, as long as the colour change of said active region is noticeable to the user of the article. Furthermore the active region can be located at the peripheral edge of the article.

Specifically, when located on or underneath the topsheet in a way such that the colour change is noticeable through the topsheet, the active region can for instance be located at or around the central zone of the absorbent article, i.e. the zone with the highest probability of being exposed to body fluids. The active region can be comprised by either one interconnected region or by a number of separate sub regions. For instance, a sanitary napkin has an active region as described before around the central zone of the topsheet, which is comprised of four sub regions, one is oriented towards each longitudinal end of the napkin and one is oriented towards each lateral end of the napkin. Another option is a sanitary napkin having a 1 cm wide active region around its whole circumference, i.e. along its whole peripheral edge. It would be completely obvious for the skilled artisan in the field of sanitary absorbent articles for feminine hygiene to arrange the active region herein in further fashions, serving the purpose of the present invention in a like manner.

The active region and the sub regions can have numerous shapes and sizes. They can be open or filled circles or ellipsoids, or straight or bent lines, dots, squares or rectangles or the like. The can extend across the whole length and/or width of the article or only across part thereof. It is also within the scope of the present invention that the active region extends across the whole topsheet and/or backsheet. Exemplary embodiments are listed hereinafter.

In one embodiment the topsheet and/or secondary topsheet is provided with a thermochromic dye close to its peripheral edge. In the central area of the topsheet or secondary topsheet there is no thermochromic dye present. In this configuration the thermochromic dye functions as a loading indicator indicating with a colour change that the maximum capacity of the article because of the fact that body fluids are excreted at the internal body temperature of 37° C., which is maintained for some time after excretion. Because the skin and thus the absorbent article is cooler than the interior of the body there is a change of temperature occurring when body fluid is excreted to the article. This change of temperature leads to a colour change of the thermochromic dye when the peripheral regions of the article are wetted. This colour change can be detected by the wearer, indicating that the absorbent article has reached its maximum capacity in terms of fluid absorption and should be changed accordingly. It is know from colour theory that the effect of a certain colour to the human eye is increased when its complementary colour is in adjacency. Therefore it is beneficial to use a thermochromic dye, which changes to a colour between blue and green (ideally cyan) upon change of temperature, as the red colour of blood is the complementary one. Timely changing the absorbent article aids the prevention of leakage of body fluids into the undergarments of the user.

In another embodiment the topsheet and/or secondary topsheet is provided with a photochromic dye, which changes to a colour between green and blue (ideally cyan) when exposed to light for masking body fluids excreted onto the topsheet. According to colour theory mixing a colour with its complementary colour leads to mutual weakening of both colour's effect to the human eye. This effect is often referred to as "greying out". Masking of fluids, especially blood and menses, is of particular applicability in geographies, where the requirements of consumers in terms of personal hygiene are particularly high.

Another embodiment utilizing photochromic dyes is a sanitary napkin, where all artwork and printings on the topsheet is done by photochromic materials, which are substantially uncoloured when not exposed to light and that become coloured when exposed to light. This provides an unexpected fancy effect to the consumer and underlines the sophisticated technology of the absorbent article. Besides pure artwork such printings can also have a function, such as aiding the correct positioning of the article.

An exemplary embodiment of an absorbent article of the present invention using piezochromic dyes is a sanitary pad, i.e. a panty liner, being provided with a piezochromic material along its periphery. The piezochromic dye becomes coloured upon being exposed to a pressure and thus functions as a positioning indicator indicating whether or not the article was positioned correctly by identifying zones of excessive pressure to the user. Ideally the exertion of stresses should occur to the article in an even, symmetrical manner. Consequently, when the article is worn correctly, the piezochromic dye has changed its colour in same symmetrical fashion. Otherwise, when the article is worn improperly the piezochromic dye will change colour asymmetrically over the extension of the article.

'Colour change' herein means that at least a part of the absorbent article or the bag, wherein the absorbent article is packaged, which part is visible from outside of the article or bag, changes its colour in response to an external stimulus. The colour change is noticeable from outside said article.

'Colour change material' herein means a material contained in the active region of the absorbent article or the bag, which provides the colour change in response to the external stimulus. Specifically, the colour change material changes its own colour upon exposure to such a stimulus in a way, which is noticeable from outside said article. The colour change material can be 'thermochromic', which means that the colour change is induced by a change of temperature, or 'photochromic', which means that the colour change is induced by light, or 'piezochromic', which means that the colour change is induced by pressure applied. These definitions comprise materials changing colour irreversibly, reversibly or quasi-reversibly in response to the respective stimulus. Thermochromic materials herein also comprise pseudo-thermochromic materials showing a hysteresis of thermochromism. Combinations of the aforementioned mechanisms in the colour change material are also within the scope of the present invention. The colour change materials herein can either be coated onto parts of the absorbent article or bag, such as on films or fibres, or can form an integral part of components of the absorbent article or bag by being added e.g. to the polymeric master batch these components are made of.

A colour change 'noticeable from outside the article' as used herein means that the colour change is noticeable to the naked human eye at least when the article is unworn. In other words, the article does not require to be disassembled for notification of the colour change.

'External stimuli' as used herein refers to the exposure of the absorbent article to energy from outside the article in the form of pressure, temperature, light or combinations thereof.

Colour Change Materials

The colour change materials herein change their colour in response to external stimuli as defined hereinbefore. Colour change materials suitable herein perform a colour change, which is noticeable for at least some seconds after triggering.

a) Thermochromic Materials

Thermochromic materials are known e.g. from Kirk-Othmer Encyclopedia $3^{rd}$ edition, vol. 6, p. 130, or from U.S. Pat. No. 5,389,093. Any formulation containing thermochromic materials can be used herein, as long as it meets health and safety requirements applicable here.

Thermochromic materials can be applied as a coating as illustrated e.g. in JP 7,034,394 or U.S. Pat. No. 5,221,288, or can form an integral part of the materials used to make the absorbent article. The latter possibility includes addition of thermochromic materials to the masterbatch of polymers as described in EP 610,072. Another possibility of applying thermochromic materials to the article is as a laminar covering in the form of a painting or ink as described in U.S. Pat. No. 4,121,011 or U.S. Pat. No. 4,826,550. The thermochromic materials used can be in the form of fine pigments particles, microencapsulated materials, molecular materials and the like.

Most thermochromic dyes undergo a colour change from a specific colour to colourless in a reversible manner. There are also so-called low temperature thermochromic dyes, which change their colour from colourless at room temperature to a certain colour upon being cooled. Background colour pigments can be provided in combination with the thermochromic materials such that when the thermochromic material changes to colourless the background pigment becomes dominant for the colour. For example if a yellow background pigment is mixed with a red thermochromic material the visible colour will change from orange to yellow at the temperature the thermochromic materials changes colour.

Thermochromic materials are marketed e.g. by Sunchemical and Clariant. Exemplary classes of thermochromic materials suitable herein are liquid crystals and leucodyes. Preferably both classes of materials are encapsulated in suitable microcapsules.

Liquid crystals are very sensitive to temperature changes and change colour even in a temperature range of 0.1° C., typically from black to a colour. Application of liquid crystals requires highly specialized printing.

Leucodyes typically change colour in a temperature increment of 3–6° C., in most cases from coloured to clear (uncoloured). The benefit of leucodyes is that they can be easily applied by printing or by admixing in the polymer masterbatch.

Another example of photochromic materials suitable herein are dye crystals, such as those marketed by Chromatic Technologies, Inc. These materials are uncoloured in the shadow and become coloured when exposed to sunlight, particularly UV radiation. The UV radiation causes chemical changes in the dye crystal. There are both reversibly and irreversibly colour changing materials available. Suitable application techniques of dye crystals is ink printing or admixing into polymeric masterbatches.

b) Piezochromic Materials

Any piezochromic materials disclosed in the art are suitable herein as long as they meet health and safety requirements applicable here. An example is disclosed in U.S. Pat. No. 6,330,730.

In one example the piezochromic material is thermochromic and responds to a temperature increase caused by pressure applied. In another example the piezochromic material comprises a dye, which is encapsulated into microcapsules. Upon application of pressure these capsules break and release the dye, which then becomes visible. The colour intensity is directly linked to the amount of pressure applied. Typical piezochromic materials require a pressure of from 14 to 140 kPa.

Most typically piezochromic colour change materials change their colour in an irreversible fashion after exertion of pressure. This is due to the fact that the colour change was achieved by the destruction of microcapsules, in which the substances for achieving the colour change were encapsulated.

c) Photochromic Materials

Photochromic materials are known e.g. from Kirk-Othmer Encyclopedia $3^{rd}$ edition, vol. 6, p. 121. Any formulation containing thermochromic materials can be used herein, as long as it meets health and safety requirements applicable here.

Absorbent articles or bags for packaging absorbent articles according to the present invention can comprise one or more photochromic materials. The photochromic materials can be in the form of fine pigment particles or dyes. Examples for photochromic materials suitable herein are described in U.S. Pat. No. 6,306,409; U.S. Pat. No. 6,080,415 or U.S. Pat. No. 5,730,961.

Photochromic colour change materials most typically change their colour in a reversible fashion upon change of lighting.

Optional Components of the Absorbent Article

The sanitary napkin may contain a fragrance activated by body temperature. The sanitary napkin may alternatively contain a fragrance activated by body humidity or body fluid. This can be realized by encapsulating the fragrance in water-soluble microcapsules or microcapsules, which melt at body heat.

In another example the sanitary napkin contains ruptureable microcapsules dispersed therein. The microcapsules are ruptured by mechanical stress (under pressure). In a specific example the sanitary napkin contains ruptureable microcapsules between two surfaces, such as sheets or opposed faces of a folded single sheet of coated paper which are temporarily bonded by means of an adhesive (PFA) with ruptureable microcapsules dispersed therein. The microcapsules are ruptured by pulling apart the sheets (i.e. release paper) which causes the capsules to rupture and release the ingredients contained therein. By selecting the relative physical properties of the sheet, adhesive, capsules and the binding forces amongst them, a high rate of capsule rupturing can be obtained consistently.

EXAMPLES a) Thermochromic Colour Change

A sanitary napkin, commercially available under the trade name ALWAYS®, was modified by applying thermochromic dye to the peripheral edge of the secondary topsheet in a continuous 3 mm wide stripe. The thermochromic dye was obtained from Sun Chemical under the trade name Switch Blue 27 Conc, article number 308796.

b) Photochromic Colour Change

A sanitary napkin, commercially available under the trade name ALWAYS®, was modified by applying photochromic dye to the peripheral edge of the secondary topsheet in a continuous 3 mm wide stripe. The thermochromic dye was obtained from CTI Chromatic Technology under the trade name UV Flexo.

c) Piezochromic Colour Change

A sanitary napkin, commercially available under the trade name ALWAYS®, was modified by applying piezochromic dye to the peripheral edge of the secondary topsheet in a continuous 3 mm wide stripe. The thermochromic dye was obtained from SPI Sensor Products Inc. under the trade name PRESSUREX®.

The examples described above can be modified by placing the colour change materials between the backsheet, which most typically is at least translucent, and the layer directly adjacent to the backsheet, typically the absorbent core. By this the colour change is noticeable through the backsheet of the absorbent article. In further variations of the examples described here the colour change material is placed such that the colour change is noticeable through the topsheet and through the backsheet, e.g. by placing colour change material between the backsheet and the directly adjacent layer and on the topsheet or secondary topsheet.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for feminine hygiene comprising at least one active region, wherein said active region constitutes at least a portion of said article and is provided with a color change material, wherein said color change material changes color in response to an external stimulus and wherein the color change is noticeable from outside said article, wherein said stimulus is selected from at least one of change of temperature, exertion of pressure and exposure to light, wherein said article releases a perfume simultaneously with said color change.

2. An absorbent article for feminine hygiene comprising at least one active region, wherein said active region constitutes at least a portion of said article and is provided with a color change material, wherein said color change material changes color in response to an external stimulus and wherein the color change is noticeable from outside said article, wherein said stimulus is exertion of pressure and the color change material is selected from liquid encapsulated dyes; or mixtures of dyes and encapsulated decolorizers; or mixtures of a color precursor and encapsulated colorizers; or mixtures thereof.

* * * * *